United States Patent [19]

Zomer et al.

[11] Patent Number: 5,374,534
[45] Date of Patent: Dec. 20, 1994

[54] METHOD OF PREPARING D-LUCIFERIN DERIVATIVES

[75] Inventors: Eliezer Zomer, Quincy; Steven Saul, Arlington; Stanley E. Charm, Boston, all of Mass.

[73] Assignee: Charm Sciences, Inc., Malden, Mass.

[21] Appl. No.: 62,315

[22] Filed: May 14, 1993

Related U.S. Application Data

[60] Division of Ser. No. 7,572, Jan. 22, 1993, abandoned, which is a division of Ser. No. 818,782, Jan. 9, 1992, Pat. No. 5,283,180, which is a continuation-in-part of Ser. No. 556,952, Jul. 19, 1990, Pat. No. 5,200,311.

[51] Int. Cl.$^5$ .................... C12Q 1/66; C12Q 1/00; A61K 37/02; C07D 277/62
[52] U.S. Cl. .......................... 435/8; 435/4; 435/25; 435/7.72; 435/23; 540/469; 548/178; 536/26.26; 530/330
[58] Field of Search .................. 435/8, 25, 7.72, 4, 435/23; 540/469; 548/178; 436/546; 536/24; 530/330

[56] References Cited

U.S. PATENT DOCUMENTS

| | | | |
|---|---|---|---|
| 4,286,057 | 8/1981 | Wulff et al. | 435/8 |
| 4,357,420 | 11/1982 | Bostick et al. | 435/8 |
| 4,863,689 | 9/1989 | Leong et al. | 422/52 |
| 5,035,999 | 7/1991 | Geiger et al. | 435/23 |
| 5,098,828 | 3/1992 | Geiger et al. | 435/7.72 |
| 5,200,311 | 4/1993 | Charm et al. | 435/4 |

OTHER PUBLICATIONS

Toya, Y. et al, "Improved synthetic methods of firefly luciferin derivatives for use in bioluminescent analysis of hydrolytic enzymes; carboxylic esterase and alkaline phosphatase", Bulletin of the Chemical Society Of Japan, vol. 65, No. 10, Oct. 1992 pp. 2604–2610.

Kamijo, T. et al, "1-acyl-3-substituted imidazolium salts as highly reactive acylating agents", Chemical And Pharmaceutical Bulletin, vol. 30, No. 10, Oct. 1992, pp. 4242–4244.

Primary Examiner—Michael G. Wityshyn
Assistant Examiner—Louise N. Leary
Attorney, Agent, or Firm—Richard P. Crowley

[57] ABSTRACT

A method of preparing a 6-substituted D-luciferin ester suitable for use in the determination of pesticides by a bioluminescence method. The 6-substituted D-luciferin esters, such as 6-D-luciferin acetate, are prepared in a liquid solvent containing N-acetyl imidazole with D-luciferin and recovering as the reaction product 6-D-luciferin acetate.

10 Claims, No Drawings

METHOD OF PREPARING D-LUCIFERIN DERIVATIVES

REFERENCE TO PRIOR APPLICATIONS

This application is a divisional application of U.S. Ser. No. 08/007,572, filed Jan. 22, 1993, now abandoned, which application was a divisional application of U.S. Ser. No. 07/818,782, filed Jan. 9, 1992, now U.S. Pat. No. 5,283,180, issued Feb. 1, 1994, which patent is a continuation-in-part of U.S. Ser. No. 07/556,952, filed Jul. 19, 1990, now U.S. Pat. No. 5,200,311 issued Apr. 6, 1993.

The parent application concerns a radio assay test method employing $C^{14}$ radiolabeled materials which includes adding insect brain tissue, such as bee or housefly brain tissue homogenate, to a test sample containing an organophosphate or carbamate pesticide which interacts with the brain homogenate. The admixture is incubated and then a radiolabeled substrate, for example, a $C^{14}$ substrate, is added to interact with the remaining sites in the incubated insect brain homogenate and the mixture incubated. The resulting incubated test sample, brain homogenate and radiolabeled substrate is then separated to provide a liquid fraction sample to which is added a scintillation material. The radioactivity of the separated fraction is then determined by counts per minute and compared with a standard or control to determine the concentration of the pesticide in the test sample.

BACKGROUND OF THE INVENTION

Different kinds of organisms (arthropods, avians, mammals) are sensitive to pesticides. Pesticides are generally classified as herbicides, fungicides and insecticides. Pesticides interact with their nervous and enzymatic systems. Such toxicants may bind to binders (ion channels) located on the nerve cells, or to enzymes located around them and elsewhere. Pesticides also interact with various protective mechanisms, such as degrading enzymes and non-specific binders.

The brain and the nerve system of insects in general were the target for insecticides since their early development (1940s) for pest control in agriculture and human health. Pesticides that target the insect brain as the site of action usually display rapid action and require low dosage for good control.

Since the early 1970s, attempts have been made to use in vitro brain preparation to study the mode of action of pesticides. Only limited studies were reported on using this method for monitoring pesticides. Lack of stability and sensitivity as compared with the traditional gas chromatography (GC) or mass spectrometry made this early attempt useless. The use of color reaction requires high enzyme and substrate concentration to monitor brain preparation activity and the results were insensitive assays. The enzymes used were taken through laborious purifications, and it was found that only a limited spectrum of pesticides could be detected. Apparently, the source and the purified preparation were of limited sensitivity and for only a few pesticides which made it unsuitable as a monitoring and screening assay.

In recent years, bioluminescence or chemiluminescence has been used to detect extremely small quantities of material. Assays using these signals have been developed to measure substrates, such as ATP or NADH, and enzymes, such as alkaline phosphatase. Advantages to using bioluminescence as an assay system is the sensitivity of the reaction and the speed in which that reaction can be measured. For example, the bioluminescence reaction with the enzyme luciferase catalyzes the reaction between luciferin and ATP to produce light in milliseconds.

It is desirable to test for the concentration of pesticides in various materials, such as soil and water for health and safety purposes. In particular, it is desirable to provide an effective test kit and method to determine the concentration level of organophosphate and carbamate pesticides at low levels, such as below 50 ppb and even as low as 5 ppb. Specific organophosphate insecticides may be tested employing antibodies, but these have limited use as broad spectrum screening methods. Herbicides may be tested on a specific basis by chromogenic enzyme-based test methods, but such tests do not provide accurate results at low concentration levels and are susceptible to color interpretation.

Therefore, a new, accurate, effective test kit and method for the determination of pesticides, such as organophosphate and carbamate pesticides, are desirable.

SUMMARY OF THE INVENTION

The invention relates to a test kit and method for the determination of pesticides. In particular, the invention concerns a chemiluminescence or bioluminescence test method and test kit for the determination of organophosphate and carbamate-type pesticides at levels below about 50 ppb.

A test kit and method has been developed for the rapid, generally 10 to 15 minutes, and sensitive, less than 50 ppb or lower, method for the multiple detection of organophosphate and carbamate pesticides in water, soil, food (e.g. meat, fish, fruits and vegetables) and other materials. The test method employs an insect brain preparation having a mixture of receptors or enzymes with sites that interact with the pesticides and particularly that react or interact with organophosphate and carbamate pesticides. The pesticides alter or cause a significant reduction in the brain activities of the insect brain preparation which are inversely correlated with the amount of the pesticide present in the test sample. The activity is measured by employing tracer analogs or substrates which upon exposure to the insect brain preparation are altered chemically and/or physically and the changes monitored by a light emission reaction. The activities can be chemical as in an enzymatic reaction or physical as in receptor binding.

For example, in one embodiment in an enzymatic reaction, the hydrolysis of a luciferin derivative to luciferin by a brain preparation has been found to be extremely sensitive to organophosphates and carbamates. The luciferin liberated by the reaction is oxidized by the enzyme luciferase and adenosine triphosphate (ATP), an energy donor, and emits light measured as bioluminescence or chemiluminescence. The bioluminescence or chemiluminescence emitted is measured and monitored at a low level and high speed employing a luminometer or scintillation counter. The assay is carried out in three simple steps of a short incubation period, e.g. 2 to 10 minutes, of the test sample and the brain preparation; addition of a substrate tracer or pesticide analog tracer, such as a luciferin derivative with additional incubation, e.g. 2 to 5 minutes; and the measurement directly or after a separation step to obtain liquid fraction for light emission by activation with the enzyme (luciferin-luciferase). The general assay preparation is illustrated in Table 1.

Therefore, a test method has been found for the determination of pesticides which are sensitive to insect brain preparation and particularly organophosphate and carbamate pesticides. The test method comprises incubating a mixture of a test sample and an insect brain preparation; adding to the incubated mixture a D luciferin derivative, such as, but not limited to: D luciferin acetate, a novel compound whose hydrolysis is inhibited in the presence of the pesticide; incubating the test sample, brain preparation and D luciferin derivative mixture to liberate luciferin; admixing a portion of the incubated D luciferin derivative-containing admixture with ATP and luciferase as a reaction mixture to provide an oxidized luciferin (oxyluciferin) and emitted luminescence; measuring the emitted luminescence, for example, with a luminometer; and determining the concentration of the pesticide in the test sample by comparison of the emitted, measured luminescence of a standard or of a control sample.

The test kit for the determination of pesticides comprises in combination an insect brain preparation which is sensitive to the pesticide, e.g. bee brain homogenate, a D luciferin derivative which is inhibited in hydrolysis in the presence of the pesticide, such as D luciferin acetate; the enzyme luciferase and ATP to form a reaction mixture when added together to the incubated test sample, brain preparation and D luciferin derivative. The test kit may include those standard articles of laboratory equipment and chemicals, like buffers, needed to carry out and measure the results to include, but not be limited to: incubation dishes or plates and an incubation water bath, etc.; buffers; a luminometer to measure emitted luminescence; a standard control chart or graph of luminescence vs. pesticide concentration for comparison and determination of the pesticide concentration; and separating equipment, such a chromatographic column or ultrafiltration membrane to obtain a liquid fraction of the incubated mixture.

A wide variety of insect brain tissue material may be used in the test method of the invention, such as the crude, stabilized brain tissue, particularly the homogenate of arthropods, for example, but not limited to: bees; beetles; aphids; mosquitoes; silkworms; mites; blow flies; and houseflies (*Musca domestica*) alone or in combination.

Brain preparations from various sources have differences in specificity for pesticides. Therefore, it is important to obtain one or more brain preparations which will react with a broad spectrum of pesticides for monitoring purposes. Insects as the target for pesticides are one of the best sources for brain preparations. Specificity and sensitivity can vary from one insect to another. Bees were chosen as a preferred choice for their known sensitivity to a variety of insecticides. It was found that bee brain preparation was approximately 2 to 4 logs more sensitive in the bioluminescence assay system than any previously reported assay system.

One novel D luciferin derivative suitable for use in the pesticide test method comprises 6-acetyl D luciferin or luciferin acetate, a novel compound, as its homolog. Suitable luciferin derivatives are those 6-substituted D luciferin compounds which in the presence of insect brain preparation react to cleave the substituted ester group at the 6-position of the D luciferin derivative to provide D luciferin for further reaction with ATP and luciferase to produce luminescence which can be measured. The luciferin derivative 6-acetyl D luciferin is prepared by reacting D luciferin with excess acetyl imidazole in a solvent, e.g. water-solvent solution which acetylates D luciferin under mild conditions with about 100% efficiency to provide the 6-acetyl D luciferin.

It has been found that both organophosphate and carbamate pesticides inhibit the hydrolysis of D acetyl luciferin by insect brain preparations. There are significant advantages in the use of a D luciferin derivative, like D luciferin acetate, as a substrate in the test method. There is an unusual, unexpected, high specificity of the bee or silkworm brain preparations toward D luciferin acetate and only small quantities of the D luciferin acetate are required for the assay. For example, the concentration of D luciferin acetate in the incubation mixture may be as low as $1 \times 10^{-11}$ moles or less and the assay sensitivity for luciferin is 1 to $5 \times 10^{-13}$ moles. The assay time is about 10 minute in total. While D luciferin acetate has been found to be a preferred D luciferin derivative for use in the test method, other D luciferin derivatives with similar reactions may be employed. Those luciferin derivatives disclosed in the publication of the *Journal of Clinical Chemistry and Chemical Biochemistry* entitled "Synthesis and Characterization of Luciferin Derivatives for Use in Bioluminescence-Enhanced Enzyme Immunoassay New Ultrasensitive Detection Systems for Enzyme Immunoassay", Miska et al, J. Clin Chem Clin Biochem 25(1) 1987, pp. 23–30, are not suitable for use in the test method and include specifically D-luciferin methyl ester, D-luciferyl-L-phenylalanine, D luciferyl-L-Na-arginine, D-luciferin-O-sulphate and D-luciferin-O-phosphate.

To test the ability of the assay system to monitor for the presence of pesticides in food, six apples from different sources were tested. Of the six apples, four apples were positive and two apples were negative. The four positive apples were obtained from local orchards, while the negative apples were purchased from local supermarkets. Local water was also tested and was found marginal positive. Table 3 gives detection levels expected in water for 15 different organophosphate and carbamate pesticides.

Test Procedure Used for Organophosphate and Carbamate Pesticides

1. Sample is preincubated with a predetermined quantity (dilution 1:200) of brain preparation for 5 minutes.
2. Luciferin acetate (200 pmoles) is added to the incubation mixture for additional 5 minutes.
3. A portion of this incubation mixture (100 µl) is withdrawn and added to the luciferase and ATP reaction mixture (1 ml).
4. Bioluminescence reading for 2–5 seconds is monitored.
5. The reading of the pesticide sample is compared to the control sample to quantitate the percent inhibition of the sample (see Tables 3, 4, 5 and 6).

The invention will be described for the purposes of illustration only in connection with certain embodiments; however, it is recognized that those persons skilled in the art may make various improvements, additions, changes and modifications to the illustrated embodiments all falling within the spirit and scope of the invention.

DESCRIPTION OF THE EMBODIMENTS

A. Synthesis of luciferin acetate (6-acetyl D luciferin)

Dissolve 2 mg sodium D-luciferin (purified from firefly) into 2 ml water, or dissolve 2 mg synthetic D-luciferin into 2 ml methanol as stock 3.3 mM luciferin solutions in an amber vial. Take 25 $\mu$l of either stock solution and add it to 1 ml distilled water in an amber microcentrifuge tube to get an 82.5 $\mu$M solution of luciferin. Dissolve 60 mg of N-acetylimidazole into 1.0 ml acetone to get a 545 mM solution of N-acetylimidazole. Add 30 $\mu$l of 545 mM solution of N-acetylimidazole to the 82.5 $\mu$M aqueous solution of luciferin. Mix several times and monitor the decrease of bioluminescence as the reaction continues to completion. The reaction is complete when bioluminescence can no longer be observed when using the above reaction mixture as a source for luciferin. Keep solution on ice. The concentration of N-acetylimidazole in this reaction mixture is 16.35 mM or approximately 200 times the concentration of luciferin.

Notes: D-Luciferin from firefly was purchased from Sigma. Synthetic D-luciferin was purchased from Boehringer Mannheim. Also, a D-luciferin is available from Bio-Orbit. Luciferin stock solution from Sigma was dissolved in water while D-luciferin stock solution from Boehringer or Bio-Orbit was dissolved in methanol. N-acetylimidazole was purchased from Sigma. The reaction described above was performed in 1 ml and 1 concentration range, but it could be scaled up using a larger volume size. Other derivatives of luciferin, such as luciferin phosphate, luciferin sulfate, luciferin arginine have been described in the literature, but to our knowledge, luciferin acetate has not been described, nor to our knowledge has it been used in a coupled reaction with brain extract to monitor pesticides.

B. Preparation of Insect Brain Extract

Insects are stored from at $-20°$ C. or below. Insect heads are collected by dissection with a scalpel and placed in a 50 ml beaker containing approximately 15 ml ice cold 0.07 M phosphate buffer, pH 7.0, containing 1 mM EDTA (ethylenediaminetetra acetic acid) and 1 $\mu$M phenylthiourea. The insect heads are gently homogenized at low speed in a Tekmar Tissumizer. Aliquots of this crude extract are transferred to microcentrifuge tubes and centrifuged. The supernatant is retained and applied to a sephadex G-25 column equilibrated with 0.07 M phosphate buffer, pH 7.0, containing 1 mM EDTA and 1 $\mu$M phenylthiourea. Fractions are collected every 2 minutes and monitored for esterase activity using luciferin acetate as a substrate and measuring bioluminescence. Fractions with esterase activity are pooled and used as the insect head extract for use in the pesticide assay.

Notes: Brain extracts have been prepared primarily from honey bees, but also has been extracted from silkworm and blowflies. Protein concentration of the bee head extract is between 2 to 5 mg/ml. For the assay, 5 to 10 $\mu$l is used per assay.

C. Bioluminescence Reaction

1. Reaction buffer for bioluminescence: Weigh out 4.48 g tricine, 0.6 g magnesium sulfate, 0.146 g EDTA, 100 mg bovine serum albumin, and 77 mg dithiothreitol into 600 ml water. Adjust pH to 7.8 with 10% sodium hydroxide and add distilled water to 1 liter.

2. Luciferase preparation: For luciferase (1 mg) from firefly purchased from Boehringer Mannheim dissolve in 1 ml 0.5 M Tris-acetate buffer, pH 7.5, and let stand 30 minutes. Portion out 40 $\mu$l of this solution into glass test tubes and freeze at $-20°$ C. Redissolve frozen stock with 1 ml bioluminescence buffer. For luciferase purchased from Bio-Orbit take 3 mg and dissolve in 1 ml bioluminescence buffer. Each luciferase solution is kept on ice. For each bioluminescent assay, a 30 $\mu$l aliquot from either luciferase solution described above is used. For the Boehringer luciferase, approximately 1 $\mu$g enzyme is used for each assay.

3. ATP Preparation: ATP (adenosine 5'-triphosphate) is preweighed from Sigma and contains 1 mg ATP and 40 mg magnesium sulfate. To this vial add 10 ml water and 100 $\mu$l 1.0 M HCl and vortex. ATP solution is kept on ice. The stock solution is 1.8 mM and for each bioluminescent assay, 30 $\mu$l is used for a final concentration of 54 $\mu$M.

4. Luciferin Acetate: Take 100 $\mu$l 82.5 $\mu$M solution of luciferin acetate prepared as described above in section A and 900 $\mu$l distilled water and add to amber microcentrifuge tube. This solution is 8.25 $\mu$M. For pesticide assays, a 25 $\mu$l portion of the 8.25 $\mu$M solution is added to 2 ml 0.07 M phosphate buffer, pH 7.0, to give a 0.1 $\mu$M concentration of luciferin acetate. A 100 $\mu$l portion of this solution is withdrawn and incubated with 1 ml of the bioluminescent buffer. Final concentration is approximately 10 nM luciferin acetate or 10 pmoles luciferin acetate.

5. Bioluminescence Measurement: A 1 ml portion of the bioluminescent buffer is added to a $13 \times 100$ mm test tube. A 100 $\mu$l portion of the luciferin acetate solution (0.1 $\mu$M) is withdrawn and added. Then 30 $\mu$l aliquots of the luciferase and ATP solutions are added to the test tube. The test tube is vortexed and the bioluminescence measured after 2 to 5 seconds using a luminometer. The bioluminescence reading with luciferin acetate will be negative. If luciferin is measured at 10 pmoles then the reading in the luminometer will be approximately 100,000. If the concentration of any of the reagents described above is increased, then the light reading will be increased. Although the present concentrations give acceptable values, the concentration of the reagents may be altered to give optimal performance. The above liquid reagents may also be immobilized in individual tablet form to provide stability and consistency to the reagents, such as in compressed tablet form with inert cellulosic fillers.

D. Assay of Pesticides Using Bioluminescence

1. To $13 \times 100$ mm test tubes add 2 ml 0.07 M phosphate buffer, pH 7.0. Add 25 $\mu$l positive pesticide control (organophosphate and/or carbamate pesticide), 25 $\mu$l water to negative control tube and 25 $\mu$l of test sample to another tube. If test sample contains solvent other than water, then use this solvent as the negative control tube.

Note: Although 25 $\mu$l is indicated above, the volume size of sample could be less or greater as long as brain activity is not affected by the solvent.

2. Add insect brain extract (5 or 10 $\mu$l depending on activity) to the 2 ml incubation mixture in step 1, vortex and incubate at $35°$ C. in temperature block for 10 minutes. Use timer with alarm to monitor time.

3. At 10 minutes, add 25 $\mu$l 8.25 $\mu$M luciferin acetate solution to 2 ml incubation mixture in step 2. Reset timer to zero and restart timer.

4. At 5 minutes, take 100 μl portion from each sample. Use separate pipette tip for each sample and add the 100 μl portion to separate 13×100 mm test tubes containing 1 ml of bioluminescence buffer.

Note: In this reaction, the sample is withdrawn after 5 minutes. Since the reaction is kinetic, the concentration of luciferin formed in the reaction will increase with time. Therefore, the time an aliquot can be withdrawn can vary as long as it is in the linear section of the curve, and aliquots from samples are withdrawn at the same time.

5. Add 30 μl ATP solution followed by 30 μl luciferase solution to one of the assay tubes in step 4. Vortex and measure bioluminescence for 2 to 5 seconds. Record value and proceed to the next tubes as above.

6. Zero control bioluminescence reaction will be uninhibited by pesticide and will have a high bioluminescence reading. In the positive samples the esterolitic activity of the bee extract will be inhibited and less luciferin will form giving a low bioluminescent reading. Divide sample reading or positive control by zero control and multiply to 100 to get percent inhibition.

Note: The source for some of the chemicals used has been set forth; however, other suppliers can supply these chemicals and therefore, the procedure is not reliant on any one source for a particular reagent except for the preparation of luciferin acetate.

Tables 5-11 represent test data showing the increase in bioluminescence as a function respectively of time, luciferase, ATP, luciferin acetate and bee head brain preparation in the test assay.

TABLE 1

Schematic of Pesticide Assay

1. BE$^{a)}$ + pesticide$^{b)}$ $\xrightarrow{35° C.}$ BE − pesticide + BE
   (brain extract)

2. D luciferin derivative$^{c)}$ $\xrightarrow{BE}$ D luciferin + luciferin derivative 3. ATP + luciferin $\xrightarrow{Luciferase}$
   (adenosine triphosphate)

oxyluciferin + pyrophosphate + AMP(adenosine monophosphate) + luminescence (to be measured)$^{d)}$ Legend
$^{a)}$for example, insect bee brain homogenate
$^{b)}$organophosphate and carbamate pesticides
$^{c)}$for example, D luciferin acetate
$^{d)}$luminometer

TABLE 2

PREPARATION OF D LUCIFERIN ESTER

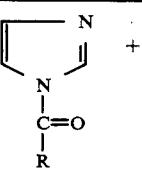

ACYLATED IMIDAZOLE

D LUCIFERIN

TABLE 2-continued

PREPARATION OF D LUCIFERIN ESTER

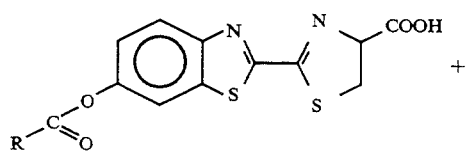

D LUCIFERIN ESTER

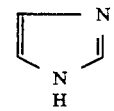

IMIDAZOLE

LEGEND
"R" IS AN ALKYL GROUP OR PHENYL GROUP, e.g. $C_1-C_6$

TABLE 3

Charm Pesticide Assay for Organophosphate and Carbamate Inhibition of Bee Brain Activity for Ac-luciferin

| Pesticide | $I_{50}^{a)}$ (ppb) |
|---|---|
| Carbamates | |
| Methomyl | 4 |
| Propoxur | 10 |
| Carbofuran | 8 |
| Bendocarb | 12 |
| Organophosphates | |
| Mevinphos | 2 |
| Ethion | 2 |
| Chlorpyros | 1 |
| Phorate | 2 |
| Malathion | 6 |
| Oxydemeton-methyl | 1 |
| Disulfoton | 5 |
| Methyl parathion | 1 |
| DDVP | 0.004 |
| Naled | 0.05 |
| Diazinon | 15 |

$^{a)}I_{50}$ is the concentration of inhibitor which gives a 50% decrease in enzymatic activity as measured by bioluminescence.

TABLE 4

Inhibition of Silkworm Brain Activities by Various Organophosphate Pesticides at 25 PPB

| Pesticide | % Inhibition |
|---|---|
| Phorate | 50.5 |
| Naled | 98.0 |
| Methyl parathion | 0 |
| Ethion | 77.0 |
| Oxydemeton-methyl | 0 |
| Diazinon | 0 |
| DDVP | 100.0 |
| Disulfoton | 25 |
| Mevinphos | 50 |

TABLE 5

Inhibition of Bee Brain Extract by Organophosphates As a Function of Pesticide Concentration

| Methyl Parathion | | Phorate | | Chlorpyrifos | |
|---|---|---|---|---|---|
| ppb | % activity | ppb | % activity | ppb | % activity |
| 0 | 100 | 0 | 100 | 0 | 100 |
| 0.625 | 62 | 1.25 | 70 | 0.625 | 68 |
| 1.25 | 40 | 2.5 | 29 | 1.25 | 34 |
| 2.5 | 23 | 3.125 | 23 | 2.50 | 24 |
| 5.0 | 15 | 6.25 | 8 | 3.125 | 13 |

TABLE 5-continued

Inhibition of Bee Brain Extract by Organophosphates As a Function of Pesticide Concentration

| Ethion | | Diazinon | | Oxydemeton-methyl | |
|---|---|---|---|---|---|
| ppb | % activity | ppb | % activity | ppb | % activity |
| 0 | 100 | 0 | 100 | 0 | 100 |
| 0.3125 | 84 | 25 | 40 | 0.3125 | 90 |
| 0.625 | 71 | 50 | 45 | 0.625 | 43 |
| 1.25 | 65 | 100 | 28 | 1.25 | 47 |
| 2.5 | 37 | | | 2.5 | 37 |
| | | | | 25.0 | 21 |

| Disulfoton | | Mevinphos | | Malathion | |
|---|---|---|---|---|---|
| ppb | % activity | ppb | % activity | ppb | % activity |
| 0 | 100 | 0 | 100 | 0 | 100 |
| 3.125 | 66 | 0.3125 | 64 | 6.25 | 53 |
| 6.25 | 47 | 0.625 | 52 | 12.5 | 50 |
| 12.5 | 35 | 1.25 | 48 | 25.0 | 27 |
| 25.0 | 19 | 2.5 | 24 | 50.0 | 27 |
| | | 3.125 | 12 | | |
| | | 6.25 | 9 | | |

| DDVP | | Naled | |
|---|---|---|---|
| ppb | % activity | ppb | % activity |
| 0 | 100 | 0 | 100 |
| 0.0013 | 74 | 0.031 | 50 |
| 0.0023 | 49 | 0.625 | 29 |
| 0.0028 | 60 | 0.125 | 30 |
| 0.0057 | 52 | 0.250 | 25 |
| 0.011 | 25 | | |

TABLE 6

Inhibition of Bee Brain Extract by Carbamates As a Function of Pesticide Concentration

| Bendiocarb | | Methomyl | | Carbofuran | |
|---|---|---|---|---|---|
| ppb | % activity | ppb | % activity | ppb | % activity |
| 0 | 100 | 0 | 100 | 0 | 100 |
| 12.5 | 50 | 3.125 | 45 | 6.25 | 59 |
| 25 | 26 | 6.25 | 16 | 12.5 | 41 |
| 50 | 18 | 12.5 | 20 | 25 | 32 |
| 100 | 11 | 25.0 | 12 | 50 | 22 |

| Propoxur | |
|---|---|
| ppb | % activity |
| 0 | 100 |
| 3.1 | 62 |
| 12.5 | 43 |
| 25.0 | 44 |
| 62.5 | 29 |
| 125.0 | 27 |

TABLE 7

Increase In Bioluminescence as a Function of Time Using Pesticide Assay in Control Reaction

| Time (min) | Light reading |
|---|---|
| 0 | 0 |
| 0.75 | 390 |
| 1.75 | 1230 |
| 2.75 | 3030 |
| 3.75 | 3510 |
| 5.0 | 5550 |
| 7.0 | 9360 |
| 9.0 | 11460 |
| 11.0 | 13200 |
| 14.0 | 20640 |
| 16.0 | 27300 |

TABLE 8

Increase in Bioluminescence as a Function of Luciferase Using the Pesticide Assay in Control Reaction

| Luciferase ($\mu$g) | light reading |
|---|---|
| 0 | 0 |
| 0.17 | 390 |
| 0.34 | 1200 |
| 0.5 | 1470 |
| 0.67 | 4830 |
| 0.83 | 7740 |
| 1.0 | 8580 |
| 1.17 | 17280 |
| 1.34 | 20700 |
| 1.51 | 31868 |
| 1.68 | 40140 |

TABLE 9

Increase in Bioluminescence as a Function of ATP using the Pesticide Assay in Control Reaction

| ATP ($\mu$M) | Light Reading |
|---|---|
| 0 | 0 |
| 0.9 | 390 |
| 1.8 | 1289 |
| 3.6 | 4110 |
| 5.4 | 8220 |
| 9.0 | 20760 |
| 10.8 | 24060 |

TABLE 10

Increase in Bioluminescence as a Function of Luciferin Acetate Concentration Using the Pesticide Assay in Control Reaction

| Luciferin Acetate ($\mu$M) | Light Reading (at 3 min) |
|---|---|
| 0 | 0 |
| 0.2 | 8520 |
| 0.4 | 15120 |
| 0.8 | 61680 |
| 1.6 | 180240 |
| 3.2 | 467280 |
| 6.4 | 724080 |

TABLE 11

Increase in Bioluminescence as a Function of Bee Brain Extract Concentration Using Pesticide Assay in Control Reaction

| Bee Extract ($\mu$l) | Light Reading |
|---|---|
| 0 | 0 |
| 10 | 1920 |
| 20 | 6484 |
| 40 | 22260 |
| 80 | 28880 |

What is claimed is:

1. A method of preparing a 6-substituted D-luciferin ester compound, which method consists essentially of:
   a) reacting in a liquid solvent a substituted N-acylated imidazole compound with D-luciferin; and
   b) recovering a solution of 6-substituted D-luciferin ester compound.

2. The method of claim 1 wherein the liquid solvent comprises a water solvent mixture.

3. The method of claim 1 wherein the liquid solvent comprises water.

4. The method of claim 1 wherein the substituted N-acylated imidazole compound comprises N-acetylimidazole in an acetone-water solvent.

5. The method of claim 1 which includes monitoring the decrease in bioluminescence of the luciferin as a measure of the completeness of the reaction.

6. The method of claim 1 wherein the substituted group of the N-acylated imidazole compound is selected from the group consisting of: alkyl, benzyl and phenyl radicals.

7. The method of claim 1 wherein the liquid solvent comprises methanol, and the D-luciferin is a synthetic D-luciferin.

8. The method of claim 1 wherein the N-acylated imidazole compound is N-acetyl imidazole.

9. The method of claim 8 wherein the substituted N-acylated imidazole compound is used in stoichiometric excess.

10. A method of preparing a 6-substituted acetyl D-luciferin ester compound, which method consists essentially of:
   a) reacting in a liquid solvent a stoichiometric excess of N-acetyl imidazole with D-luciferin to provide 6-acetyl-D-luciferin ester compound and imidazole; and
   b) recovering a liquid solvent solution of the 6-acetyl-D-luciferin ester compound for use in a bioluminescence test method.

* * * * *